United States Patent
Funabasama et al.

(10) Patent No.: US 10,130,316 B2
(45) Date of Patent: Nov. 20, 2018

(54) X-RAY CT APPARATUS AND DISPLAY METHOD FOR CT IMAGE

(71) Applicant: TOSHIBA MEDICAL SYSTEMS CORPORATION, Otawara-Shi (JP)

(72) Inventors: Shintaro Funabasama, Utsunomiya (JP); Takeo Nabatame, Otawara (JP)

(73) Assignee: Toshiba Medical Systems Corporation, Otawara-Shi (JP)

( * ) Notice: Subject to any disclaimer, the term of this patent is extended or adjusted under 35 U.S.C. 154(b) by 576 days.

(21) Appl. No.: 14/821,231

(22) Filed: Aug. 7, 2015

(65) Prior Publication Data
US 2015/0342544 A1 Dec. 3, 2015

Related U.S. Application Data

(63) Continuation of application No. PCT/JP2015/050298, filed on Jan. 7, 2015.

(30) Foreign Application Priority Data

Jan. 7, 2014 (JP) .................................. 2014-001228

(51) Int. Cl.
*A61B 6/12* (2006.01)
*A61B 6/04* (2006.01)
(Continued)

(52) U.S. Cl.
CPC ............. *A61B 6/12* (2013.01); *A61B 6/032* (2013.01); *A61B 6/0407* (2013.01); *A61B 6/06* (2013.01);
(Continued)

(58) Field of Classification Search
None
See application file for complete search history.

(56) References Cited

U.S. PATENT DOCUMENTS 6,445,761 B1 * 9/2002 Miyazaki ............... A61B 6/032
378/16
2012/0059251 A1 3/2012 Bakker et al.
2014/0086470 A1 3/2014 Mukumoto

FOREIGN PATENT DOCUMENTS

CN 102835970 A 12/2012
JP 2007-325787 A 12/2007
(Continued)

OTHER PUBLICATIONS

International Preliminary Report on Patentability and Written Opinion dated Jul. 12, 2016 in PCT/JP2015/050298 filed Jan. 7, 2015.
(Continued)

*Primary Examiner* — Hoon Song
(74) *Attorney, Agent, or Firm* — Oblon, McClelland, Maier & Neustadt, L.L.P.

(57) ABSTRACT

An X-ray CT apparatus includes a table-top, an X-ray tube, a detector and a processing circuitry. The processing circuitry reconstructs a CT image based on a detection signal. The processing circuitry sets a field of view based on positions of a puncture needle and a puncture target on the CT image. The processing circuitry controls an X-ray irradiation coverage based on the field of view, the X-ray irradiation coverage being an area irradiated with the X-rays. The processing circuitry displays a CT image reconstructed in the field of view on a display, after the X-rays based on the X-rays whose irradiation coverage is controlled emitted and the detection signal is outputted.

10 Claims, 17 Drawing Sheets

(51) Int. Cl.
- *A61B 6/00* (2006.01)
- *A61B 6/06* (2006.01)
- *G06T 11/00* (2006.01)
- *A61B 6/03* (2006.01)
- *A61B 10/02* (2006.01)
- *A61B 34/20* (2016.01)
- *A61B 90/11* (2016.01)
- *A61B 90/00* (2016.01)

(52) U.S. Cl.
CPC .............. *A61B 6/461* (2013.01); *A61B 6/487* (2013.01); *A61B 6/5205* (2013.01); *A61B 6/542* (2013.01); *G06T 11/005* (2013.01); *A61B 10/0233* (2013.01); *A61B 34/20* (2016.02); *A61B 90/11* (2016.02); *A61B 2090/3762* (2016.02); *G06T 2207/10081* (2013.01); *G06T 2207/30088* (2013.01)

(56) References Cited

FOREIGN PATENT DOCUMENTS

| | | |
|---|---|---|
| JP | 2012-527936 A | 11/2012 |
| JP | 2013-022155 A | 2/2013 |
| JP | 2013-111227 A | 6/2013 |
| JP | 2013-158389 A | 8/2013 |
| JP | 2013-172951 A | 9/2013 |

OTHER PUBLICATIONS

International Search Report dated Mar. 31, 2015 for PCT/JP2015/050298 filed Jan. 7, 2015 with English Translation.

Combined Chinese Office Action and Search Report dated Mar. 14, 2018 in Patent Application No. 201580000488.0 (with English language translation of categories of cited documents).

\* cited by examiner

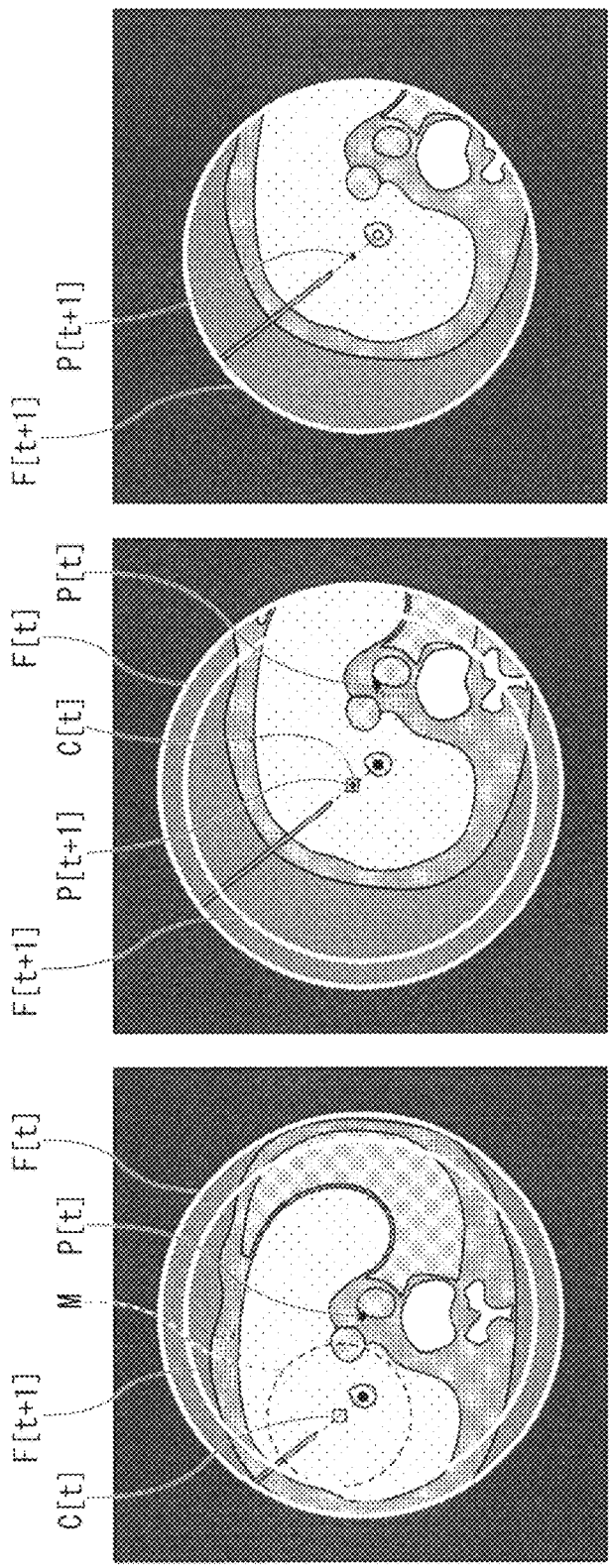

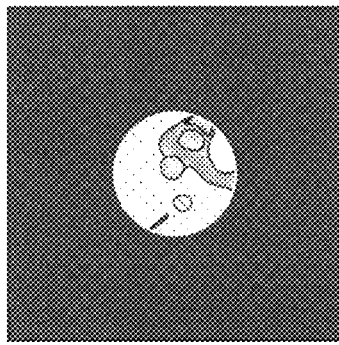
FIG. 11D  FL[18], F[18]
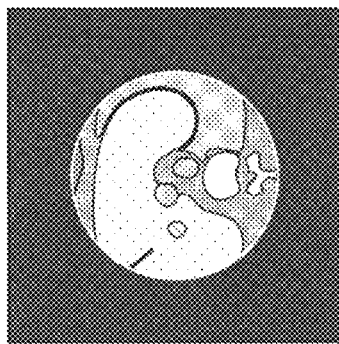
FIG. 11A  FL[8], F[8]
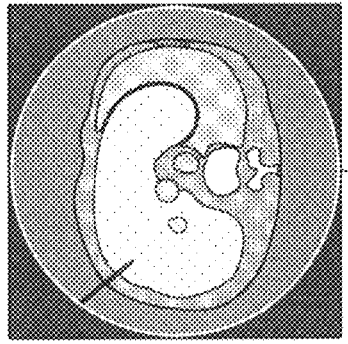
FIG. 11B  FL[5], F[5]
FIG. 11E
FIG. 11C

X-RAY CT APPARATUS AND DISPLAY METHOD FOR CT IMAGE

CROSS-REFERENCE TO RELATED APPLICATION

This application is a Continuation Application of No. PCT/JP2015/50298, filed on Jan. 7, 2015, and the PCT application is based upon and claims the benefit of priority from Japanese Patent Application No. 2014-1228, filed on Jan. 7, 2014, the entire contents of which are incorporated herein by reference.

FIELD

An exemplary embodiment as one aspect of the present invention relates to an X-ray CT apparatus and a display method for CT image adapted to generate images.

BACKGROUND

An X-ray CT (computed tomography) apparatus is an apparatus which scans an object (patient) using X-rays, processes collected data using a computer, and thereby produces images of the patient's interior. Specifically, the X-ray CT apparatus exposes the patient to X-rays multiple times from different directions along a circular orbit around the object. The X-ray CT apparatus detects the X-rays transmitted through the object and collects plural items of detection data. The collected detection data is subjected to A/D (analog to digital) conversion by a data collection unit and then sent to a console apparatus.

The console apparatus generates projection data by pre-processing the detection data. Thereafter, the console apparatus performs a reconstruction process based on the projection data and generates tomographic data as well as volume data which is based on plural items of tomographic data. The volume data is a data set which represents a three-dimensional distribution of CT values corresponding to a three-dimensional area of the object.

The X-ray CT apparatus can create an MPR (multi planar reconstruction) display by rendering the volume data in any desired direction. Hereinafter, a sectional image whose MPR display has been created by rendering volume data is sometimes referred to as an "MPR image." Examples of MPR images include an axial image which shows an orthogonal section with respect to a body axis, a sagittal image which shows a section obtained by cutting the object straight along the body axis, and a coronal image which shows a section obtained by cutting the object across the body axis. Furthermore, the MPR images may include an image (oblique image) of an arbitrary cross section in volume data. Plural MPR images generated are displayed simultaneously on a display unit or the like.

A method is available which performs computed tomography fluoroscopy (CTF) using an X-ray CT apparatus. The CT fluoroscopy is a method for obtaining CT images of a region of interest in an object in real time (sequentially) by irradiating the patient continually with X-rays. The CT fluoroscopy generates real-time CTF images by increasing a collection rate of detection data and thereby reducing the time required for a reconstruction process. For example, the CT fluoroscopy is used for localization of a puncture target in a puncture procedure.

However, with conventional techniques, which do not change a fluoroscopic coverage during a puncture procedure which uses CT fluoroscopy, even a part which is located outside a periphery of a puncture needle tip and less relevant to the puncture procedure is irradiated with X-rays, posing a problem of unnecessary exposure of the patient to X-ray radiation.

That is, as long as the fluoroscopic coverage does not change during the puncture procedure which uses CT fluoroscopy, there remains a problem from the perspective of health hazards to the patient.

BRIEF DESCRIPTION OF THE DRAWINGS

In accompanying drawings,

FIGS. 10A to 10C are diagrams for each describing sliding of the table-top and aperture adjustment of the diaphragm;

FIGS. 11A to 11E are diagrams for each describing a method for generating a superimposed image;

DETAILED DESCRIPTION

An X-ray CT apparatus a display method for CT image according to an exemplary embodiment of the present invention will be described with reference to the accompanying drawings.

To solve the above-described problems, the present embodiment provides the X-ray CT apparatus, including: a table-top on which an object is able to be placed; an X-ray tube configured to emit X-rays around the table-top; a detector configured to detect the X-rays and output a detection signal; and a processing circuitry, wherein the processing circuitry is configured to: reconstruct a CT image based on the detection signal; set a field of view based on positions of a puncture needle and a puncture target on the CT image; control an X-ray irradiation coverage based on the field of view, the X-ray irradiation coverage being an area irradiated with the X-rays; and display a CT image reconstructed in the field of view on a display, after the X-rays based on the X-rays whose irradiation coverage is controlled emitted and the detection signal is outputted.

To solve the above-described problems, the present embodiment provides the display method for CT image, including: emitting X-rays around the table-top on which an object is able to be placed; detecting the X-rays and outputting a detection signal; reconstructing a CT image based on the detection signal; setting a field of view based on positions of a puncture needle and a puncture target on the CT image; controlling an X-ray irradiation coverage based on the field of view, the X-ray irradiation coverage being an area irradiated with the X-rays; displaying a CT image reconstructed in the field of view on a display, after the X-rays based on the X-rays whose irradiation coverage is controlled emitted and the detection signal is outputted.

Note that the X-ray CT apparatus according to the present embodiment may be any of various types, including a rotate/rotate type in which an X-ray tube and detector rotate as a single unit around the object and a stationary/rotate type in which a large number of detecting elements are arranged to form a ring and only an X-ray tube rotates around the object. The present invention is applicable to any of the types. In the following description, it is assumed that the X-ray CT apparatus is of the rotate/rotate type which is currently in the mainstream.

Figure 1:
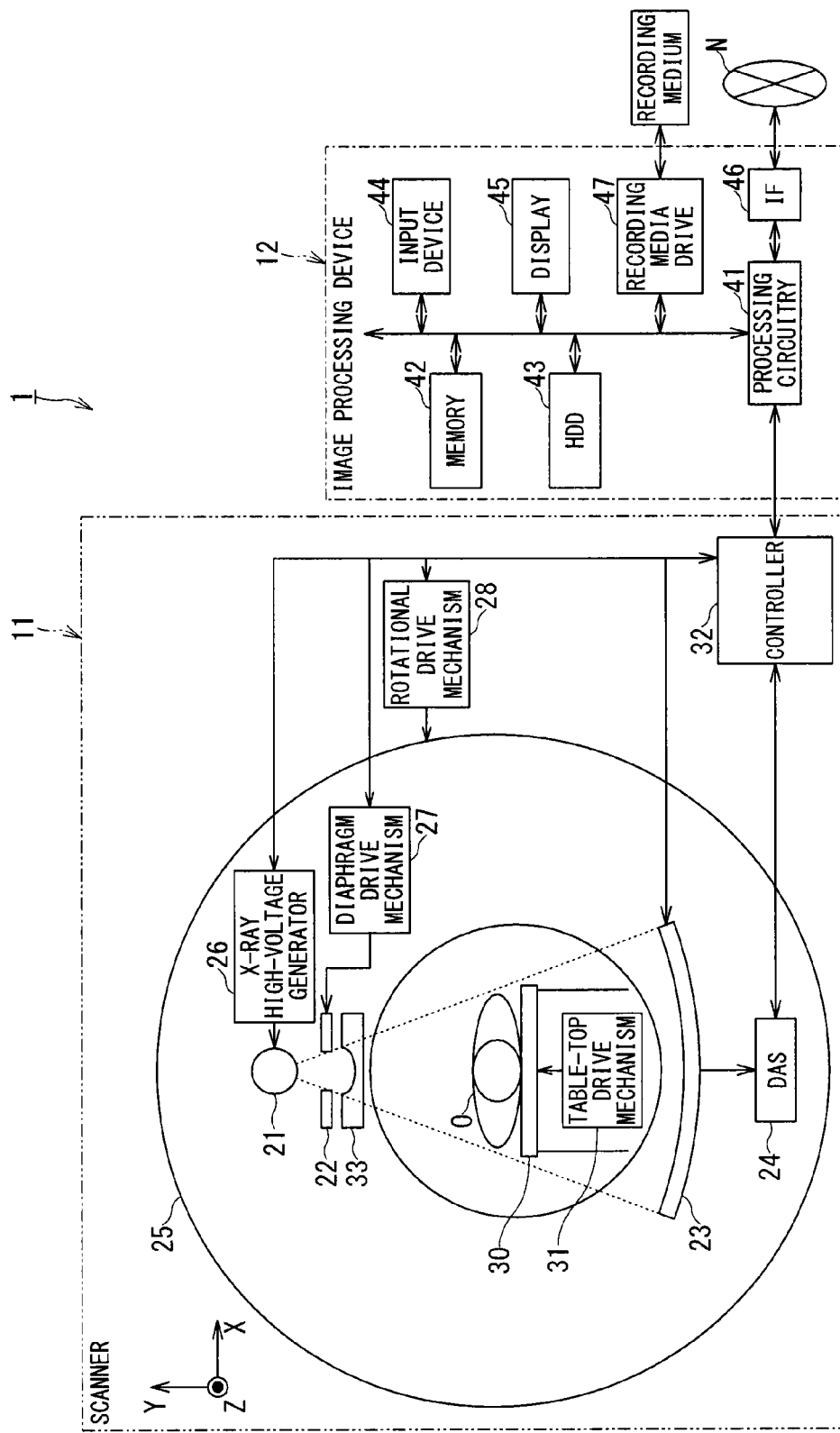
FIG. 1 is a diagram illustrating a configuration example of the X-ray CT apparatus according to a present embodiment.

FIG. 1 is a diagram illustrating a configuration example of the X-ray CT apparatus according to the present embodiment.

FIG. 1 shows the X-ray CT apparatus 1 according to the present embodiment. The X-ray CT apparatus 1 is roughly made up of a scanner 11 and an image processing device (console) 12. The scanner 11 of the X-ray CT apparatus 1 is normally installed in an examination room and configured to generate X-ray transmission data on a patient O (object). On the other hand, the image processing device 12 is normally installed in a control room next to the examination room and configured to generate projection data based on the transmission data and generate and display a reconstructed image.

The scanner 11 of the X-ray CT apparatus 1 includes an X-ray tube 21, a diaphragm (collimator) 22, an X-ray detector 23, a DAS (data acquisition system) 24, a rotary device 25, an X-ray high-voltage generator 26, a diaphragm drive mechanism 27, a rotational drive mechanism 28, a table-top 30, a table-top drive mechanism 31, a controller 32, and a wedge (X-ray beam filter) 33.

The X-ray tube 21 generates X-rays by bombarding a metal target with an electron beam at an X-ray tube voltage supplied from the X-ray high-voltage generator 26 and directs the X-rays onto the X-ray detector 23. An X-ray fan beam or X-ray cone beam is formed from the X-rays radiated from the X-ray tube 21. Electric power necessary for X-ray irradiation is supplied to the X-ray tube 21 from the X-ray high-voltage generator 26 under control of the controller 32.

Being driven by the diaphragm drive mechanism 27, the diaphragm 22 adjusts an irradiation coverage (irradiation field) of the X-rays from the X-ray tube 21. That is, by adjusting an opening of the diaphragm 22 using the diaphragm drive mechanism 27, it is possible to change the X-ray irradiation coverage in terms of a fan angle and cone angle.

Figure 2:
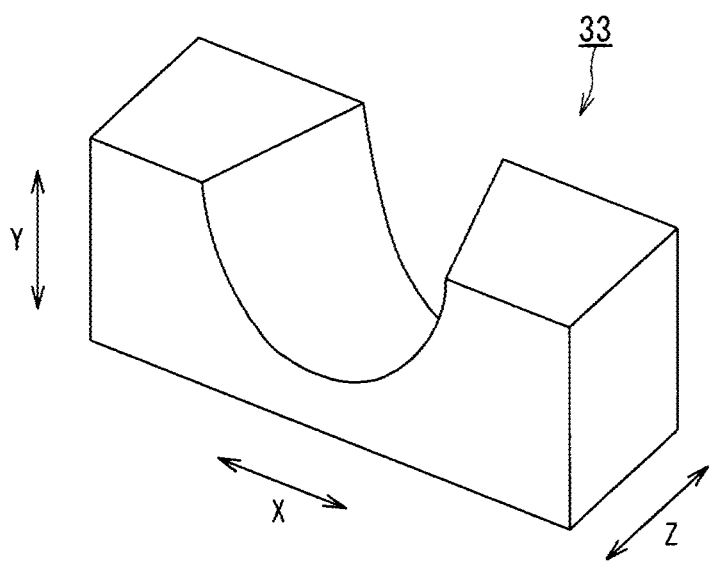
FIG. 2 is a perspective view illustrating an exemplary structure of a wedge shaped such that a width of a recess in an X direction changes gradually toward a Z direction.

The wedge 33 reduces a low-energy X-ray component before the X-rays emitted from the X-ray tube 21 passes through the patient O. Using a wedge drive apparatus (not shown), the wedge 33 adjusts a width of a recess in an X direction according to an aperture of the diaphragm 22. The wedge 33 is selected, for example, from plural wedges provided, according to the aperture of the diaphragm 22, the plural wedges having multiple types of recess. Alternatively, a single wedge 33 is provided, being shaped such that the width of the recess in the X direction changes gradually toward a Z direction. When only a single wedge is provided, the width of the recess is determined as the wedge is slid in the Z direction according to the aperture of the diaphragm 22. FIG. 2 is a perspective view illustrating an exemplary structure of a wedge shaped such that the width of the recess in the X direction changes gradually toward the Z direction.

Returning to the description of FIG. 1, the X-ray detector 23 is a one-dimensional array detector which has plural detecting elements in a channel direction and a single detecting element in a column (slice) direction. Alternatively, the X-ray detector 23 may be a two-dimensional array detector (also referred to as a multi-slice detector), in which plural detecting elements both in the channel direction and slice direction are arranged in a matrix. When the X-ray detector 23 is a multi-slice detector, data on a three-dimensional region having a width in a column direction can be collected by a single rotational scan (CT imaging and CT fluoroscopy) (volume scan). The X-ray detector 23 detects the X-rays emitted from the X-ray tube 21.

The DAS 24 amplifies a signal of the transmission data detected by each detecting element of the X-ray detector 23, converts the signal into a digital signal, and thereby generates detection data. The detection data generated by the DAS 24 is supplied to the image processing device 12 via the controller 32 of the scanner 11. Note that when CT fluoroscopy is performed, the DAS 24 increases the collection rate of the detection data.

The rotary device 25 holds the X-ray tube 21, diaphragm 22, X-ray detector 23, DAS 24, X-ray high-voltage generator 26, and diaphragm drive mechanism 27 as an integral unit. With the X-ray tube 21 and X-ray detector 23 opposed to each other, the rotary device 25 is configured to be able to rotate the X-ray tube 21, diaphragm 22, X-ray detector 23, DAS 24, X-ray high-voltage generator 26, and diaphragm drive mechanism 27 as an integral unit around the patient O. The X-ray high-voltage generator 26 may be configured to be held by the rotary device 25. Incidentally, a direction parallel to a rotation center axis of the rotary device 25 is defined as the Z direction, and a plane orthogonal to the Z direction is defined by the X direction and a Y direction.

The X-ray high-voltage generator 26 supplies electric power necessary for X-ray irradiation to the X-ray tube 21 under the control of the controller 32.

The diaphragm drive mechanism 27 has a mechanism for adjusting the X-ray irradiation coverage in terms of the fan angle and cone angle of X-rays via the diaphragm 22 under the control of the controller 32.

The rotational drive mechanism 28 has a mechanism for rotating the rotary device 25 so as to rotate around a cavity by maintaining positional relationship with the cavity, under the control of the controller 32.

The table-top 30 allows the patient O to be placed thereon.

The table-top drive mechanism 31 has a mechanism for causing the table-top 30 to move up and down along the Y direction and move forward and backward along the Z direction, under the control of the controller 32. The rotary device 25 has an opening in a central portion and the patient O placed on the table-top 30 is inserted through the opening.

The controller 32 includes a processing circuitry, a memory and the like (not shown). On instructions from the image processing device 12, the controller 32 controls the X-ray detector 23, DAS 24, X-ray high-voltage generator 26, diaphragm drive mechanism 27, rotational drive mechanism 28, table-top drive mechanism 31, wedge drive apparatus (not shown) and the like so as to perform a scan.

The image processing device 12 of the X-ray CT apparatus 1 is configured based on a computer and is capable of intercommunicating with a network (local area network) N. The image processing device 12 is mainly made up of basic hardware, including a processing circuitry 41, a memory 42, an HDD (hard disc drive) 43, an input device 44, a display 45, and an IF (interface) 46, where the processing circuitry 41 serves as a processing circuit. The processing circuitry 41 is interconnected with individual hardware components of the image processing device 12 via a bus serving as a common signal transmission path. Note that the image processing device 12 may sometimes be equipped with a recording media drive 47.

The processing circuitry 41 means any of dedicated and general-purpose CPUs (central processing units), an application specific integrated circuit (ASIC), and a programmable logic device. The programmable logic device may be, for example, any of a simple programmable logic device (SPLD), a complex programmable logic device (CPLD), and a field programmable gate array (FPGA). The processing circuitry 41 achieves the functions shown in FIG. 3 by reading and executing programs stored in the memory 42 (or the HDD 43) or directly implemented in the processing circuitry 41.

Furthermore, the processing circuitry 41 may be configured by a single-piece processing circuitry, or an integrated processor circuitry including multiple independent processing circuitries. In the latter situation, memories 42 for recording programs may be separately provided for the respective processing circuitries. Alternatively, one memory 42 may store programs corresponding to the respective functions of circuitries.

The processing circuitry 41 is a control apparatus configured as an integrated circuit (LSI) in which an electronic circuit made up of semiconductors are enclosed in a package having plural terminals. When an operator such as a doctor enters a command by operating the input device 44, the processing circuitry 41 executes a program stored in the memory 42. Alternatively, the processing circuitry 41 executes a program stored in the HDD 43, a program installed on the HDD 43 by being transferred from a network N, or a program installed on the HDD 43 by being read out of a recording medium mounted in a recording media drive 47, where the program is executed by being loaded into the memory 42.

The memory 42 is a storage device including a ROM (read only memory), a RAM (random access memory), and the like. The memory 42 stores IPL (initial program loading), BIOS (basic input/output system), and data, and is used as a work memory for the processing circuitry 41 or used to temporarily store data.

The HDD 43 is a storage device configured with an unremovable built-in metal disk to which magnetic material has been applied by coating or vapor deposition. The HDD 43 is a storage device adapted to store data as well as programs installed on the image processing device 12, where the programs include application programs, an OS (operating system), and the like. Furthermore, the OS may provide a GUI (graphical user interface) which uses a lot of graphics in displaying information on the display 45 for an operator such as a surgeon and allows basic actions to be performed via the input device 44.

The input device 44 is a pointing device configured to be operated by the operator and send an input signal to the processing circuitry 41 according to an operator action.

The display 45 includes an image composition circuit, a VRAM (video random access memory), a display, and the like (none is shown). The image composition circuit generates composite data by combining image data with character data and the like of various parameters. The VRAM presents composite data on the display. The display, which is a liquid crystal display, CRT (cathode ray tube), or the like, displays images.

The IF 46 is made up of connectors compliant with parallel connection specifications and serial connection specifications. The IF 46 has a function to connect to a network N via a telephone line through communications control in accordance with appropriate standard and thereby allows the X-ray CT apparatus 1 to be connected to the network N.

The image processing device 12 applies a logarithmic conversion process or a correction process (pre-processing) such as sensitivity correction to the detection data (raw data) received from the DAS 24 of the scanner 11, thereby generates projection data, and stores the projection data in a storage device such as the HDD 43. Furthermore, the image processing device 12 removes scattered radiation from the pre-processed projection data. The image processing device 12 removes the scattered radiation based on values of the projection data in an X-ray exposure area, and makes scattered radiation correction by subtracting estimated scattered radiation from the projection data to be corrected, where the scattered radiation is estimated from magnitude of value of projection data to be subjected to scattered radiation correction or adjacent projection data. The image processing device 12 generates (reconstructs) scan-based CT image data based on the corrected projection data and stores the image data in a storage device such as the HDD 43 or displays the image data as CT images on the display 45.

The image processing device 12 can generate volume data by interpolating plural items of reconstructed CT image data. For reconstruction of volume data, for example, any of a cone-beam reconstruction method, multi-slice reconstruction method, and extended reconstruction method can be adopted. When a volume scan is performed using a multi-slice detector as the X-ray detector 23 as described above, the image processing device 12 can reconstruct a wide range of volume data.

Then, the image processing device 12 renders the reconstructed volume data. For example, the image processing device 12 generates pseudo three-dimensional image as CT image data by performing a volume rendering process to the volume data. The pseudo three-dimensional image is an image used to two-dimensionally display a three-dimensional structure of the patient O. Furthermore, by rendering the volume data in a desired direction, the image processing device 12 generates an MPR image as image data. The MPR image is an image which shows a desired section of the patient O. Possible MPR images include an axial image, sagittal image, and coronal image, which show three mutually orthogonal sections. Note that the image processing device 12 may generate an oblique image, which shows an arbitrary cross section, as an MPR image.

Note that when CT fluoroscopy is performed, since the collection rate of the detection data is increased, reconstruction time for the image processing device 12 is shortened. Thus, the image processing device 12 can generate real-time CT image data (CTF image data) of CT fluoroscopy.

Figure 3:
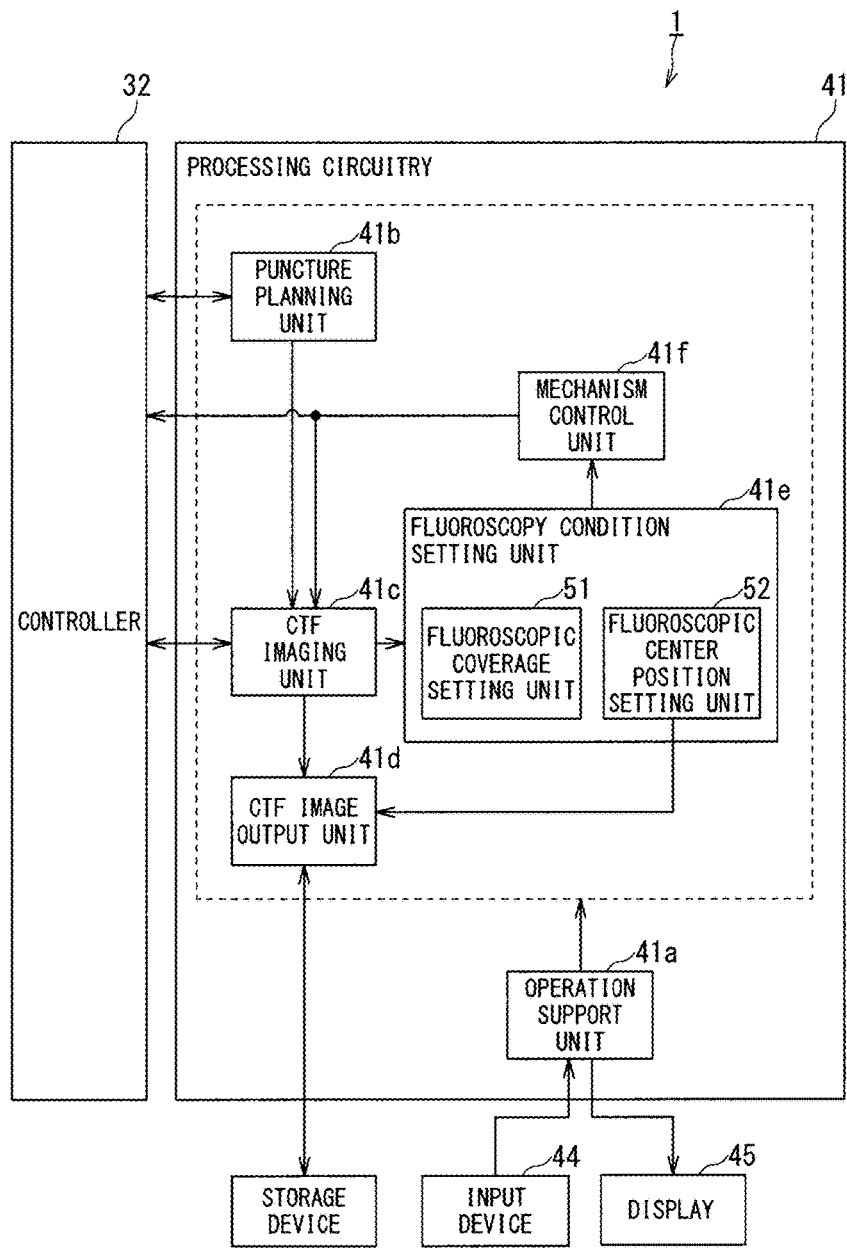
FIG. 3 is a block diagram illustrating functions of the X-ray CT apparatus according to the present embodiment.

FIG. 3 is a block diagram illustrating functions of the X-ray CT apparatus 1 according to the present embodiment.

As illustrated in FIG. 3, when the processing circuitry 41 of the X-ray CT apparatus 1 executes a program, the X-ray CT apparatus 1 functions as an operation support unit 41a, a puncture planning unit 41b, a CTF imaging unit 41c, a CTF image output unit 41d, a fluoroscopy condition setting unit 41e, and a mechanism control unit 41f. Note that all or part of the above units may be provided as hardware such as a circuit on the X-ray CT apparatus 1.

The operation support unit 41a is a user interface which uses a lot of graphics in displaying information for the operator on the display 45 and allows most of basic operations to be performed via the input device 44.

During puncture planning, the puncture planning unit 41b establishes an imaging center position which is a center position of a FOV (field of view) for CT imaging prior to CT fluoroscopy as well as a radiographic coverage which is the field of view for CT imaging. Furthermore, the puncture planning unit 41b controls the scanner 11 via the controller 32 according to the established imaging center position and thereby slides the table-top 30 (illustrated in FIG. 1), on which the patient O is placed (illustrated in FIG. 1), left or right, up or down. Furthermore, the puncture planning unit 41b controls the scanner 11 via the controller 32 according to the established radiographic coverage and thereby adjusts the aperture of the diaphragm 22 (illustrated in FIG. 1) in order to adjust the X-ray irradiation coverage.

Then, the puncture planning unit 41b causes CT imaging (single-shot imaging) to be performed at the imaging center position set after the sliding and within the radiographic coverage which is based on the aperture of the diaphragm 22 set after the aperture adjustment and generates (reconstructs) single-shot CT image data by CT imaging. Note that when the aperture of the diaphragm 22 is adjusted, the wedge 33 (illustrated in FIG. 1) may be adjusted according to the aperture of the diaphragm 22.

In addition, on a single-shot CT image displayed based on the single-shot CT image data via the operation support unit 41a, the puncture planning unit 41b sets an insert point on skin surface as well as a puncture target (tissue) according to an input from the input device 44 via the operation support unit 41a.

Figure 4:
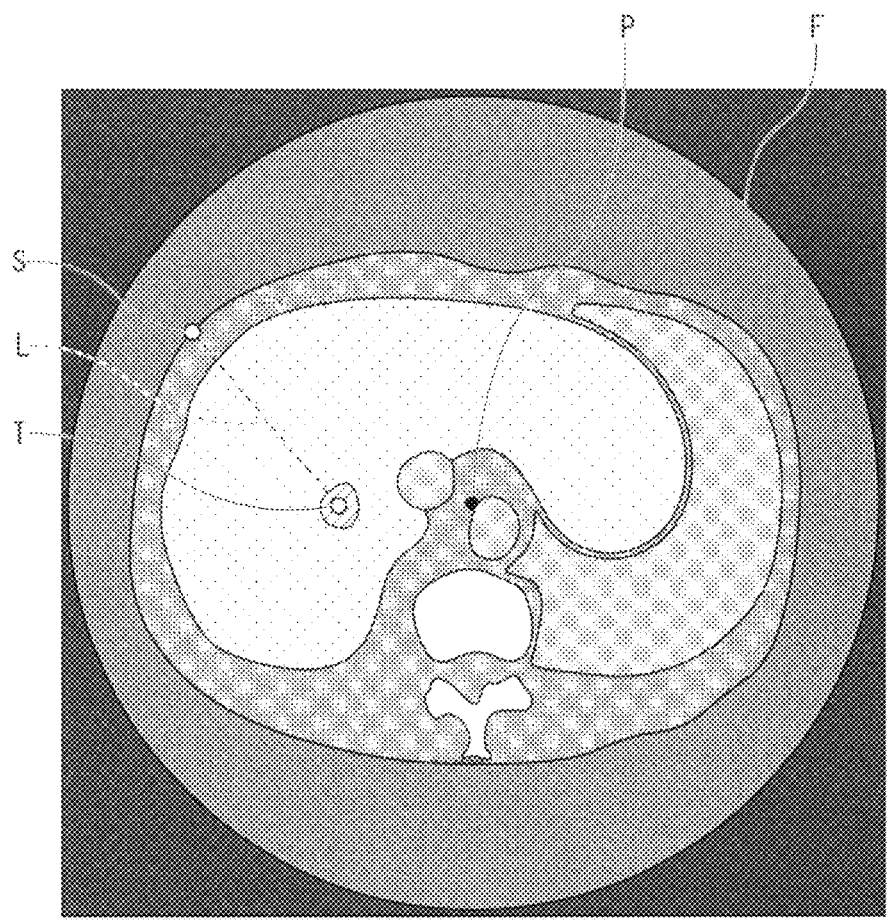
FIG. 4 is a diagram for describing a method of setting an insert point on skin surface and a puncture target.

FIG. 4 is a diagram for describing a method of setting an insert point on skin surface and a puncture target.

FIG. 4 shows a single-shot CT image which is based on single-shot CT image data corresponding to an imaging center position P and radiographic coverage F set during puncture planning as well as shows the insert point S on skin surface and puncture target set on the single-shot CT image. When the operator finishes selecting an insert point on skin surface and a puncture target via the operation support unit 41a (illustrated in FIG. 3), the insert point on skin surface and the puncture target are set on the single-shot CT image. Furthermore, a line segment (guideline) L between the insert point S on skin surface and the puncture target T may be displayed on the single-shot CT image.

Returning to the description of FIG. 3, by controlling the scanner 11 via the controller 32, the CTF imaging unit 41c performs CT fluoroscopy (real-time imaging) and generates CTF image data of frames FL[t] in real time t (t=1, 2, 3, . . . ).

The CTF image output unit 41d stores the CTF image data of the frames FL[t] generated by the CTF imaging unit 41c in a storage device such as the HDD 43 as appropriate or displays the CTF image data as CT images of the frames FL[t] on the display 45 in real time.

The fluoroscopy condition setting unit 41e sets fluoroscopy conditions for CT fluoroscopy. The fluoroscopy condition setting unit 41e has at least a fluoroscopic coverage setting unit 51, and set at least a fluoroscopic coverage as a fluoroscopy condition.

The mechanism control unit 41f controls the scanner 11 (illustrated in FIG. 1) via the controller 32 according to the fluoroscopy conditions set by the fluoroscopy condition setting unit 41e.

(First Method for Setting Fluoroscopy Conditions)

With a first method for setting fluoroscopy conditions, the fluoroscopy condition setting unit 41e has only the fluoroscopic coverage setting unit 51 and sets only a fluoroscopic coverage as a fluoroscopy condition. Then, the mechanism control unit 41f controls the X-ray irradiation coverage by controlling the aperture (fan angle) of the diaphragm 22 (illustrated in FIG. 1) based on the fluoroscopic coverage set by the fluoroscopy condition setting unit 41e.

The fluoroscopic coverage setting unit 51 sets an area including a minimum coverage on the single-shot CT image (illustrated in FIG. 4) as a fluoroscopic coverage for CT fluoroscopy. The minimum coverage includes at least a tip position of a puncture needle and a puncture target on the single-shot CT image and is set automatically upon detection of the tip position of the puncture needle and the puncture target or selected arbitrarily by the operator. The fluoroscopic coverage is the field of view (FOV) for CT fluoroscopy.

The mechanism control unit 41f changes the aperture (fan angle) of the diaphragm 22 (illustrated in FIG. 1) based on the fluoroscopic coverage set by the fluoroscopic coverage setting unit 51 and thereby controls the X-ray irradiation coverage.

FIGS. 5A, 5B, 6A, and 6B are diagrams for each describing adjustment of the aperture of the diaphragm 22 (illustrated in FIG. 1).

Figure 5B:
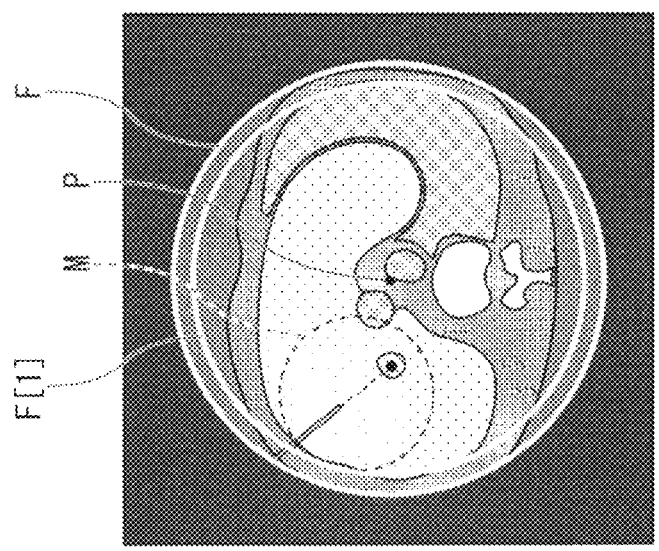
FIGS. 5A and 5B are diagrams for each describing adjustment of an aperture of a diaphragm.
Figure 5A:
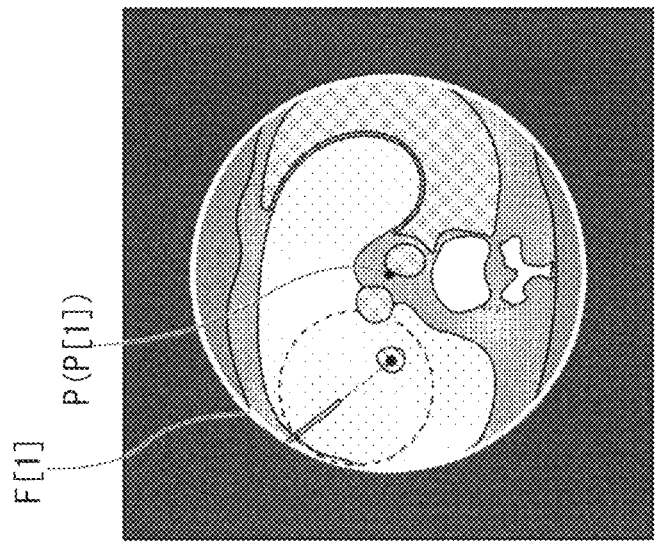

FIG. 5A shows the imaging center position P in the radiographic coverage F on a single-shot CT image illustrated in FIG. 4 as well as shows a minimum coverage M. A fluoroscopic coverage F[1] in a frame FL[1] circumscribing the minimum coverage M is determined.

Figures 6A, 6B:
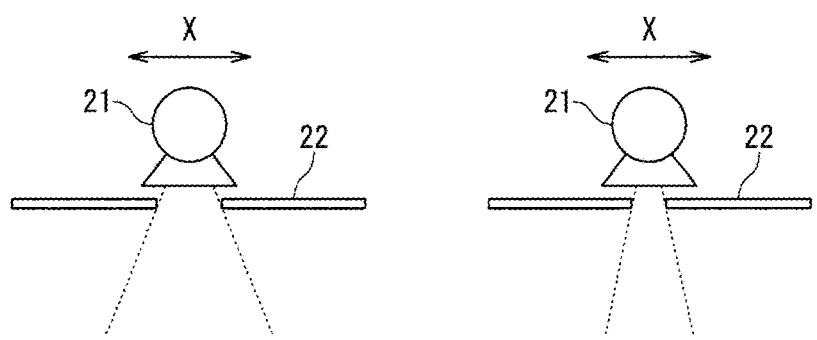
FIGS. 6A and 6B are diagrams for each describing adjustment of an aperture of the diaphragm.

In order to establish the imaging center position P illustrated in FIG. 5A as a fluoroscopic center position P[1] in the frame FL[1], position of the table-top 30 is maintained. On the other hand, in order to change the radiographic coverage F illustrated in FIG. 5A to the fluoroscopic coverage F[1], the aperture (fan angle) of the diaphragm 22 illustrated in FIG. 6A is changed to an aperture illustrated in FIG. 6B. Consequently, the fluoroscopic coverage F[1] is formed (illustrated in FIG. 5B). Then, CT fluoroscopy is started.

Note that the fluoroscopic coverage F[t] during CT fluoroscopy may be fixed to the fluoroscopic coverage F[1] or may be changed as appropriate depending on size of the minimum coverage M, which in turn is changed depending on the tip position of the puncture needle.

FIGS. 5A, 5B, 6A, and 6B show a case in which the table-top 30 (illustrated in FIG. 1) is not permitted to slide during CT fluoroscopy. In that case, the mechanism control unit 41f only adjusts the aperture of the diaphragm 22 (illustrated in FIG. 1) without sliding the table-top 30 (illustrated in FIG. 1). In addition to the aperture adjustment of the diaphragm 22, the mechanism control unit 41f may adjust the wedge 33 (illustrated in FIG. 1).

(Second Method for Setting Fluoroscopy Conditions)

With a second method for setting fluoroscopy conditions, the fluoroscopy condition setting unit 41e has a fluoroscopic center position setting unit 52 as well as the fluoroscopic coverage setting unit 51. The fluoroscopy condition setting unit 41e sets a fluoroscopic center position and fluoroscopic coverage as fluoroscopy conditions. Furthermore, the fluoroscopy condition setting unit 41e sets a center position of a minimum coverage or position of a puncture target as the fluoroscopic center position. Then, the mechanism control unit 41f controls the X-ray irradiation coverage by controlling the aperture of the diaphragm 22 (illustrated in FIG. 1) based on the fluoroscopic coverage set by the fluoroscopy condition setting unit 41e and controls the position of the table-top 30 (illustrated in FIG. 1) by controlling operation of the table-top drive mechanism 31 (illustrated in FIG. 1) based on the fluoroscopic center position set by the fluoroscopy condition setting unit 41e.

The fluoroscopic center position setting unit 52 sets the center position of the minimum coverage or position of the puncture target on the single-shot CT image (illustrated in FIG. 4) as the fluoroscopic center position for CT fluoroscopy.

The fluoroscopic coverage setting unit 51 sets the minimum coverage on the single-shot CT image (illustrated in FIG. 4) or an area including the minimum coverage as the fluoroscopic coverage for CT fluoroscopy.

The mechanism control unit 41f controls the fluoroscopic center position by sliding the table-top 30 (illustrated in FIG. 1) based on the fluoroscopic center position set by the fluoroscopic center position setting unit 52 and controls the X-ray irradiation coverage by changing the aperture (fan angle) of the diaphragm 22 (illustrated in FIG. 1) based on the fluoroscopic coverage set by the fluoroscopic coverage setting unit 51.

Figure 7B:
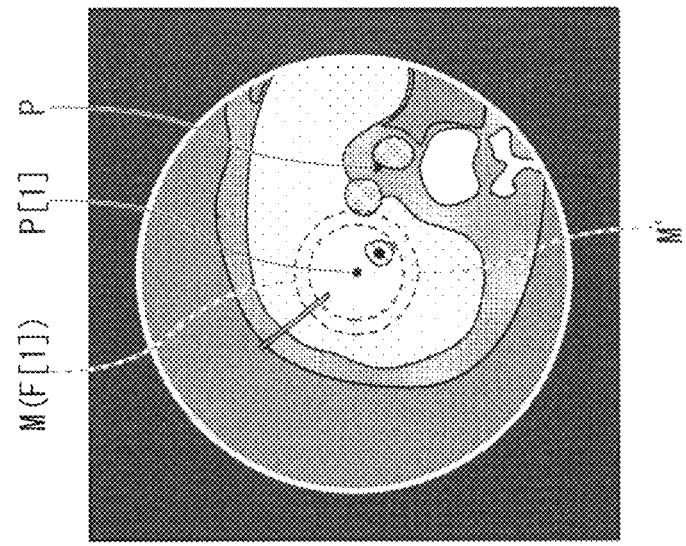
FIGS. 7A and 7B are diagrams for each describing sliding of a table-top and aperture adjustment of the diaphragm.
Figure 7A:
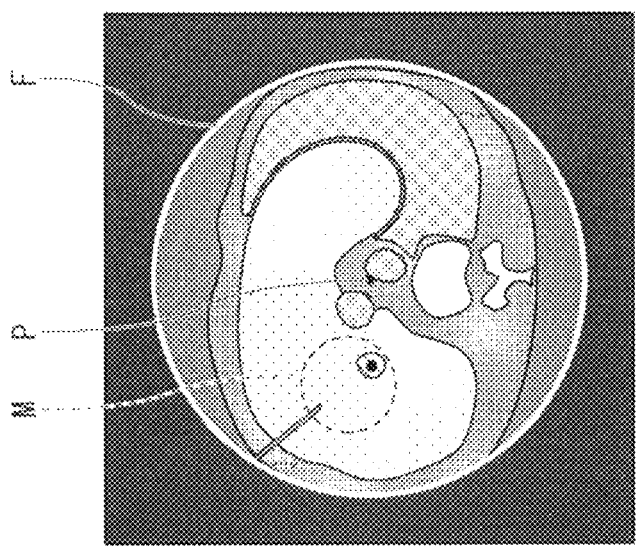

FIGS. 7A and 7B are diagrams for each describing sliding of the table-top 30 (illustrated in FIG. 1) and aperture adjustment of the diaphragm 22 (illustrated in FIG. 1).

FIG. 7A shows the imaging center position P in the fluoroscopic coverage F on the single-shot CT image illustrated in FIG. 4 as well as shows a minimum coverage M. In order to change a center position P of the minimum coverage M illustrated in FIG. 7A to the fluoroscopic center position P[1] (illustrated in FIG. 7B) in the frame FL[1], the table-top 30 is slid. Furthermore, in order to change the minimum coverage M illustrated in FIG. 7A to the fluoroscopic coverage F[1] in the frame FL[1], the aperture of the diaphragm 22 is changed. Consequently, the fluoroscopic coverage F[1] is formed (illustrated in FIG. 7B). Then, CT fluoroscopy is started.

Note that a coverage M' (concentric circle) obtained by adding a margin to the minimum coverage M illustrated in FIG. 7A may be set as the fluoroscopic coverage F[1] in the CT fluoroscopy.

Moreover, the fluoroscopic coverage F[t] during CT fluoroscopy may be fixed to the fluoroscopic coverage F[1] or may be changed as appropriate depending on the size of the minimum coverage M (or coverage M'), which in turn is changed depending on the tip position of the puncture needle.

FIGS. 7A and 7B show a case in which the table-top 30 (illustrated in FIG. 1) is permitted to slide during CT fluoroscopy. In that case, the mechanism control unit 41f slides the table-top 30 (illustrated in FIG. 1) and adjusts only the aperture of the diaphragm 22 (illustrated in FIG. 1). In addition to the aperture adjustment of the diaphragm 22, the mechanism control unit 41f may adjust the wedge 33 (illustrated in FIG. 1).

(Third Method for Setting Fluoroscopy Conditions)

With a third method for setting fluoroscopy conditions, the fluoroscopy condition setting unit 41e has the fluoroscopic coverage setting unit 51 and the fluoroscopic center position setting unit 52. The fluoroscopy condition setting unit 41e sets a fluoroscopic center position and fluoroscopic coverage as fluoroscopy conditions. Furthermore, the fluoroscopy condition setting unit 41e sets the position of the puncture target as the fluoroscopic center position. Then, the mechanism control unit 41f controls the X-ray irradiation coverage by controlling the aperture of the diaphragm 22 (illustrated in FIG. 1) based on the fluoroscopic coverage set by the fluoroscopy condition setting unit 41e and controls the position of the table-top 30 (illustrated in FIG. 1) by controlling operation of the table-top drive mechanism 31 (illustrated in FIG. 1) based on the fluoroscopic center position set by the fluoroscopy condition setting unit 41e.

When a distance between the tip position of the puncture needle and the puncture target ("T" illustrated in FIG. 4) set by the puncture planning unit 41b on the CTF image of a required frame FL[t] is smaller than a distance between the tip position and puncture target on the CTF image of the previous frame FL[t−1] (or single-shot CT image), the fluoroscopy condition setting unit 41e shrinks the fluoroscopic coverage in the frame FL[t] for CT fluoroscopy in subsequent frames FL. That is, the fluoroscopy condition setting unit 41e shrinks the fluoroscopic coverage with decreasing distance between the tip position of the puncture needle and the puncture target (with the movement of the puncture needle toward the puncture target).

Specifically, the fluoroscopic center position setting unit 52 detects the tip position of the puncture needle in the frame FL[t]. Furthermore, the fluoroscopic center position setting unit 52 calculates a middle point of a line segment between the detected tip position and a position corresponding to the position of the puncture target ("T" illustrated in FIG. 4) set by the puncture planning unit 41b. Note that the tip position of the puncture needle in the frame FL[t] is detected by image recognition of conventional technique based on the CTF image data generated by the CTF imaging unit 41c or detected by a magnetic sensor (not illustrated) attached to the puncture needle.

Figure 8:
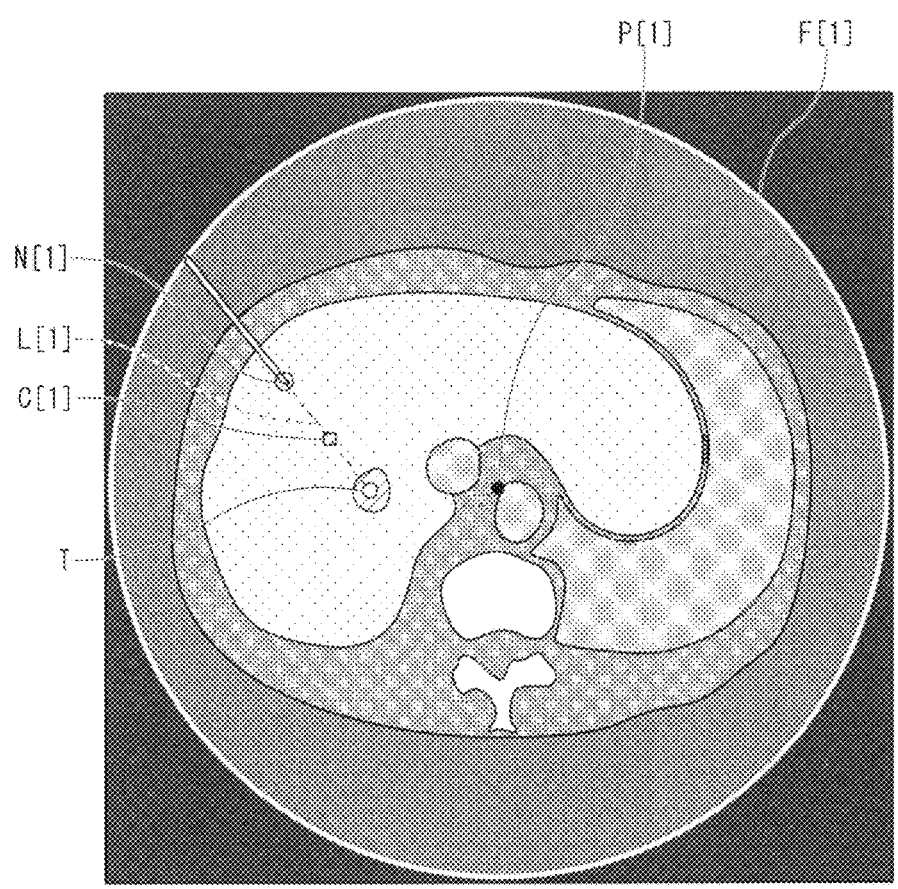
FIG. 8 is a diagram for describing a method of calculating a middle point of a line segment between a tip position of a puncture needle and a position of the puncture target in a required frame.

FIG. 8 is a diagram for describing a method of calculating the middle point of the line segment between the tip position of the puncture needle and the position of the puncture target in a required frame FL[t].

FIG. 8 shows a CTF image based on the CTF image data corresponding to the fluoroscopic center position P[1] and fluoroscopic coverage F[1], the CTF image data being generated in the frame FL[1] by CT fluoroscopy. Besides, a tip position N[1] of the puncture needle in the frame FL[1], the puncture target T at the position corresponding to the position of the puncture target ("T" illustrated in FIG. 4) set by the puncture planning unit 41b (illustrated in FIG. 3) and a middle point C[1] of the line segment L[1] between the tip position N[1] of the puncture needle and the puncture target T are also shown on the CTF image.

Returning to the description of FIG. 3, the fluoroscopic center position setting unit 52 sets the middle point calculated in the frame FL[t] as a fluoroscopic center position for the subsequent frames FL. The fluoroscopic center position setting unit 52 can set the fluoroscopic center position in the frames FL subsequent to the frame FL[t]. In the following description, it is assumed that the fluoroscopic center position setting unit 52 sets the middle point calculated in the frame FL[t] as a fluoroscopic center position in the next frame FL[t+1], but this is not restrictive, and the calculated middle point can be set as the fluoroscopic center position in the frame FL multiple frames after the current frame FL[t].

The fluoroscopic coverage setting unit 51 sets the fluoroscopic coverage in the subsequent frames FL based on the middle point calculated in the frame FL[t] by the fluoroscopic center position setting unit 52. The fluoroscopic coverage setting unit 51 can set the fluoroscopic coverage in the frames FL subsequent to the frame FL[t]. In the following description, it is assumed that the fluoroscopic coverage setting unit 51 sets the fluoroscopic coverage in the next frame FL[t+1] based on the middle point calculated in the frame FL[t] by the fluoroscopic center position setting unit 52, but this is not restrictive, and the fluoroscopic coverage setting unit 51 can set the fluoroscopic coverage in the frame FL multiple frames after the current frame FL[t].

Now description will be given of how the fluoroscopic coverage in the next frame FL[t+1] is set by the fluoroscopic coverage setting unit 51.

Figure 9A:
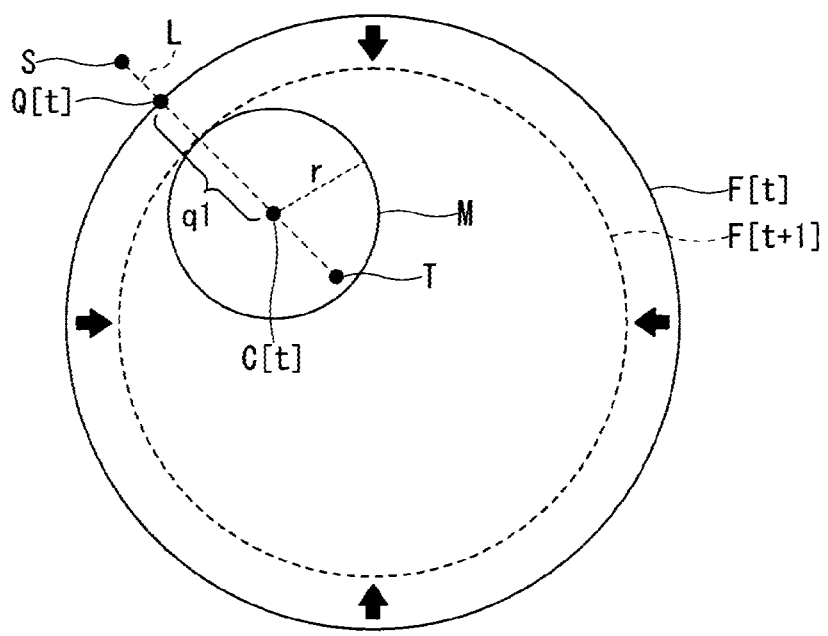
FIGS. 9A and 9B are diagrams for each describing how a fluoroscopic coverage in a next frame is set.
Figure 9B:
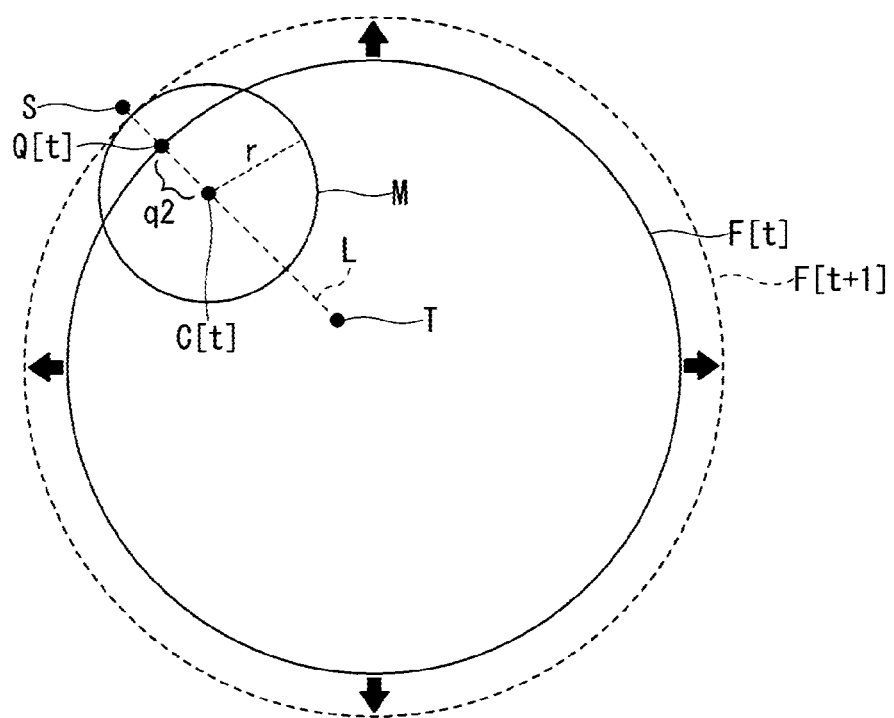

FIGS. 9A and 9B are diagrams for describing how the fluoroscopic coverage in the next frame FL[t+1] is set.

A required radius r of the minimum coverage M around a middle point C[t] illustrated in FIGS. 9A and 9B is a minimum required fluoroscopic coverage with a center at the middle point C[t] and is set arbitrarily in advance.

FIG. 9A shows the insert point S on skin surface and puncture target T set by the puncture planning unit 41b (illustrated in FIG. 3) as well as a guideline L therebetween. FIG. 9A also shows the fluoroscopic coverage F[t] in the frame FL[t], an intersection point Q[t] between the guideline L and a circumference of the fluoroscopic coverage F[t], and a distance q1 between the middle point C[t] and intersection point Q[t]. When the tip position of the puncture needle is closer to the puncture target T in the frame FL[t] than in the previous frame FL[t−1] (when the puncture needle is moving forward), the distance q1 is larger than the radius r as illustrated in FIG. 9A. In this case, the fluoroscopic coverage F[t] is shrunk such that the distance q1 will be equal to the radius r, and a fluoroscopic coverage F[t+1] circumscribing the minimum coverage M of the radius r is established.

As illustrated in FIG. 9A, when the minimum coverage M slides in a lower right direction on the guideline L with decreasing distance between the tip position of the puncture needle and the puncture target (with the movement of the puncture needle toward the puncture target T), a shrunk fluoroscopic coverage is established.

On the other hand, FIG. 9B shows the insert point S on skin surface and puncture target T set by the puncture planning unit 41b (illustrated in FIG. 3) as well as the guideline L therebetween. FIG. 9B also shows the fluoroscopic coverage F[t] in the frame FL[t], the intersection point Q[t] between the guideline L and the circumference of the fluoroscopic coverage F[t], and a distance q2 between the middle point C[t] and intersection point Q[t]. When the tip position of the puncture needle is more distant from the puncture target T in the frame FL[t] than in the previous frame FL[t−1] (when the puncture needle is moving backward), the distance q2 is smaller than the radius r as illustrated in FIG. 9B. In this case, the fluoroscopic coverage F[t] is expanded such that the distance q2 will be equal to the radius r, and a fluoroscopic coverage F[t+1] circumscribing the minimum coverage M of the radius r is established.

As illustrated in FIG. 9B, when the minimum coverage M slides in a upper left direction the guideline L with increasing distance between the tip position of the puncture needle and the puncture target (with the movement of the puncture needle away from the puncture target T), an expanded fluoroscopic coverage is established.

Returning to the description of FIG. 3, the mechanism control unit 41f adjusts the aperture of the diaphragm 22 (illustrated in FIG. 1) according to the fluoroscopic coverage in the next frame FL[t+1] set by the fluoroscopic coverage setting unit 51 of the fluoroscopy condition setting unit 41e. This allows the mechanism control unit 41f to change the fluoroscopic coverage in the frame FL[t] to the fluoroscopic coverage for the next frame FL[t+1] based on the CTF image data of the frame FL[t].

FIGS. 10A to 10C are diagrams for describing sliding of the table-top 30 (illustrated in FIG. 1) and aperture adjustment of the diaphragm 22 (illustrated in FIG. 1).

FIG. 10A shows the fluoroscopic center position P[t] and fluoroscopic coverage F[t] in the frame FL[t], the minimum coverage M based on the middle point C[t] in the frame FL[t], and the fluoroscopic coverage F[t+1] in the next frame FL[t+1] circumscribing the minimum coverage M. The table-top 30 (illustrated in FIG. 10B) is slid left or right, up or down such that the middle point C[t] illustrated in FIG. 10A will become a fluoroscopic center position P[t+1] in the next frame FL[t+1].

Furthermore, the aperture of the diaphragm 22 (illustrated in FIG. 1) is adjusted (illustrated in FIG. 10C) such that the fluoroscopic coverage F[t] illustrated in FIG. 10B will become the fluoroscopic coverage F[t+1] in the next frame FL[t+1].

Note that FIGS. 10A to 10C show a case in which the table-top 30 (illustrated in FIG. 1) is permitted to slide during CT fluoroscopy. In that case, the mechanism control unit 41f slides the table-top 30 (illustrated in FIG. 1) and adjusts only the aperture of the diaphragm 22 (illustrated in FIG. 1). In addition to the aperture adjustment of the diaphragm 22, the mechanism control unit 41f may adjust the wedge 33 (illustrated in FIG. 1).

Returning to the description of FIG. 3, when it is determined that the fluoroscopic coverage set by the fluoroscopy condition setting unit 41e in the frame FL[t] is smaller than a threshold, the CTF image output unit 41d generates superimposed CTF image data by superimposing the CTF image data which, being generated in the frame FL[t], corresponds to the fluoroscopic coverage F[t] onto the CTF image data (or single-shot CT image data) which, having been generated in a frame FL preceding the frame FL[t], corresponds to a fluoroscopic coverage larger than the fluoroscopic coverage F[t]. Then, the CTF image output unit 41d stores the superimposed CTF image data of the frame FL[t] in a storage device such as the HDD 43 as appropriate or displays the superimposed CTF image data as a superimposed image on the display 45 in real time.

Consequently, even if the fluoroscopic coverage in the frame FL[t] is smaller than the fluoroscopic coverage in a past frame, geometry around the fluoroscopic coverage in the frame FL[t] can be shown to the operator without emitting X-rays excessively.

FIGS. 11A to 11E are diagrams for describing a method for generating a superimposed image based on the CTF image data obtained by the fluoroscopy condition setting method (without any change in the fluoroscopic center position) illustrated in FIGS. 5A and 5B. In the case of FIGS. 11A to 11E, it is assumed that the table-top 30 (illustrated in FIG. 1) on which the patient O is placed (illustrated in FIG. 1) is not permitted to slide. Note that the generation of a superimposed image based on the CTF image data obtained by the fluoroscopy condition setting method (with the fluoroscopic center position changed such that the puncture target will be at a center) illustrated in FIGS. 7A to 7C and the generation of a superimposed image based on the CTF image data obtained by the fluoroscopy condition setting method (with the fluoroscopic center position changed such that a center will be at the middle point) illustrated in FIGS. 10A to 10C are equivalent to the one illustrated in FIGS. 11A to 11E.

FIG. 11A shows a CTF image based on the CTF image data in a fluoroscopic coverage F[8] in a frame FL[8]. When it is determined that the fluoroscopic coverage F[8] is smaller than the threshold, superimposed CTF image data is generated by superimposing the CTF image data which, being generated in the frame FL[8], corresponds to the fluoroscopic coverage F[8] onto the CTF image data which, having been generated in a frame preceding the frame FL[8], corresponds to a fluoroscopic coverage F[5] in a frame FL[5] illustrated in FIG. 11B, the fluoroscopic coverage F[5] being larger than the fluoroscopic coverage F[8]. The superimposed image based on the superimposed image data is illustrated in FIG. 11C. Then, in the frame FL[8], as a substitute for the CTF image (FIG. 11A) based on the CTF image data in the fluoroscopic coverage F[8] in the frame FL[8], the superimposed image illustrated in FIG. 11C is displayed.

Note that a portion outside the fluoroscopic coverage F[8] and inside the fluoroscopic coverage F[5] may be displayed in a display format different form a portion inside the fluoroscopic coverage F[8] so as to be visually recognized as a past image earlier than a time phase of the fluoroscopic coverage F[8].

FIG. 11D shows a CTF image based on CTF image data in a fluoroscopic coverage F[18] in a frame FL[18]. When it is determined that the fluoroscopic coverage F[18] is smaller than the threshold, superimposed CTF image data is generated by superimposing the CTF image data which, being generated in the frame FL[18], corresponds to the fluoroscopic coverage F[18] onto the CTF image data which, having been generated in a frame preceding the frame FL[18], corresponds to the fluoroscopic coverage F[5] in the frame FL[5] illustrated in FIG. 11B, the fluoroscopic coverage F[5] being larger than the fluoroscopic coverage F[18]. The superimposed image based on the superimposed image data is illustrated in FIG. 11E. Then, in the frame FL[18], as a substitute for the CTF image (FIG. 11D) based on the CTF image data in the fluoroscopic coverage F[18] in the frame FL[18], the superimposed image illustrated in FIG. 11E is displayed.

Note that a portion outside the fluoroscopic coverage F[18] and inside the fluoroscopic coverage F[5] may be displayed in a display format different form a portion inside the fluoroscopic coverage F[18] so as to be visually recognized as a past image earlier than a time phase of the fluoroscopic coverage F[18].

Returning to the description of FIG. 3, when it is determined that the fluoroscopic coverage set by the fluoroscopy condition setting unit 41e in the frame FL[t] is smaller than the threshold, the CTF image output unit 41d may include graphics of the puncture needle in the superimposed images (FIGS. 11C and 11E), specifically, in a portion outside the image of the CTF image data corresponding to the fluoroscopic coverage generated in the frame FL[t] and inside the image of the CTF image data corresponding to the larger fluoroscopic coverage generated in the preceding frame FL. The graphics of the puncture needle corresponds to a line segment L (illustrated in FIG. 4) set by the puncture planning unit 41b (illustrated in FIG. 3).

The CTF image output unit 41d may add information about distances to the superimposed images (FIGS. 11C and 11E), including information about a distance between the insert point S on skin surface (illustrated in FIG. 4) and puncture target T (illustrated in FIG. 4) set by the puncture planning unit 41b (illustrated in FIG. 3) and a distance between the tip position of the puncture needle and puncture target T (illustrated in FIG. 4) in the frame FL[t]. Actual distance information can be determined by converting a distance between coordinates in a screen coordinate system into a distance between coordinates in an actual physical coordinate system.

Figure 12:
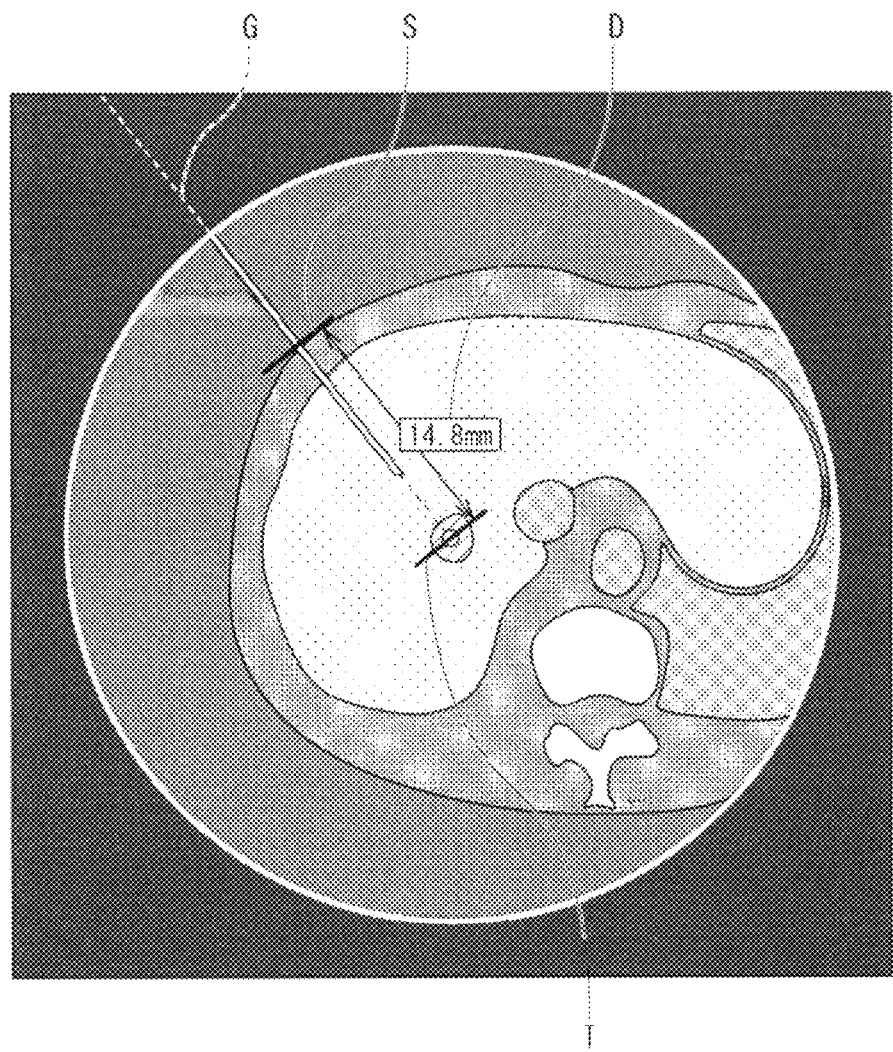
FIG. 12 is a diagram illustrating an example of the superimposed image including graphics of the puncture needle and distance information.

FIG. 12 is a diagram illustrating an example of a superimposed image which results when graphics of the puncture needle and distance information are given to the superimposed image which is based on the CTF image data obtained by the fluoroscopy condition setting method (with the fluoroscopic center position changed such that the puncture target will be at a center) illustrated in FIGS. 7A to 7C. Note that the superimposed image based on the CTF image data obtained by the fluoroscopy condition setting method (without any change in the fluoroscopic center position) illustrated in FIGS. 5A and 5B and the superimposed image based on the CTF image data obtained by the fluoroscopy condition setting method (with the fluoroscopic center position changed such that a center will be at the middle point) illustrated in FIGS. 10A to 10C are equivalent to the one illustrated in FIG. 12.

As illustrated in FIG. 12, the superimposed image includes graphics G of the puncture needle as well as distance information D about the distance between the insert point S on skin surface and the puncture target T.

Figure 13:
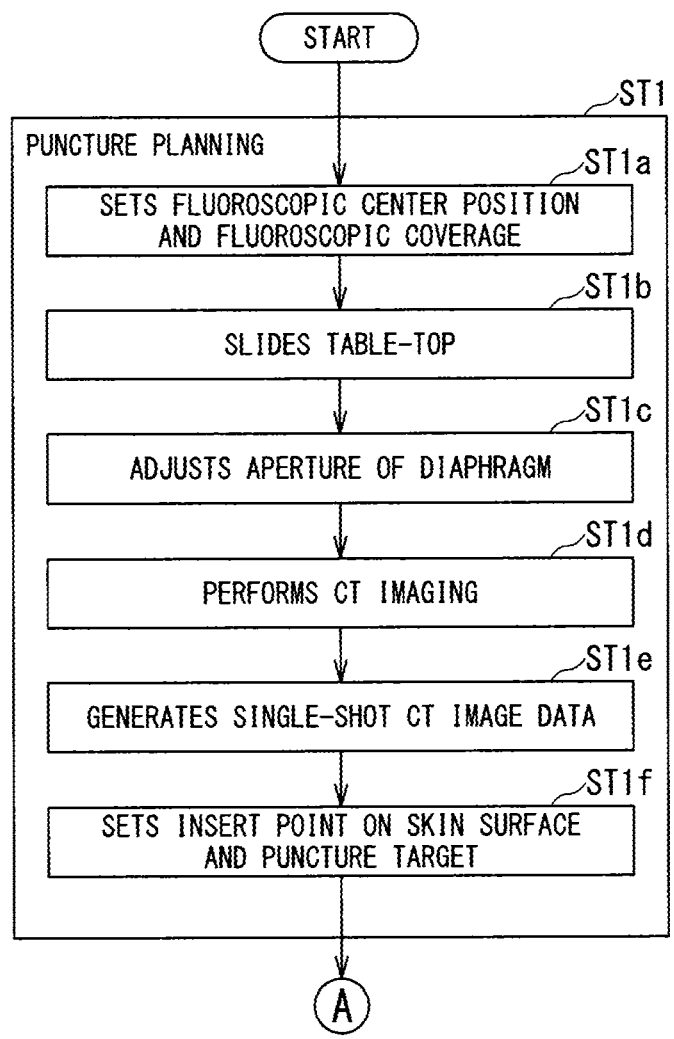
FIGS. 13 to 15 are flowcharts illustrating an operation of the X-ray CT apparatus according to the present embodiment.
Figure 14:
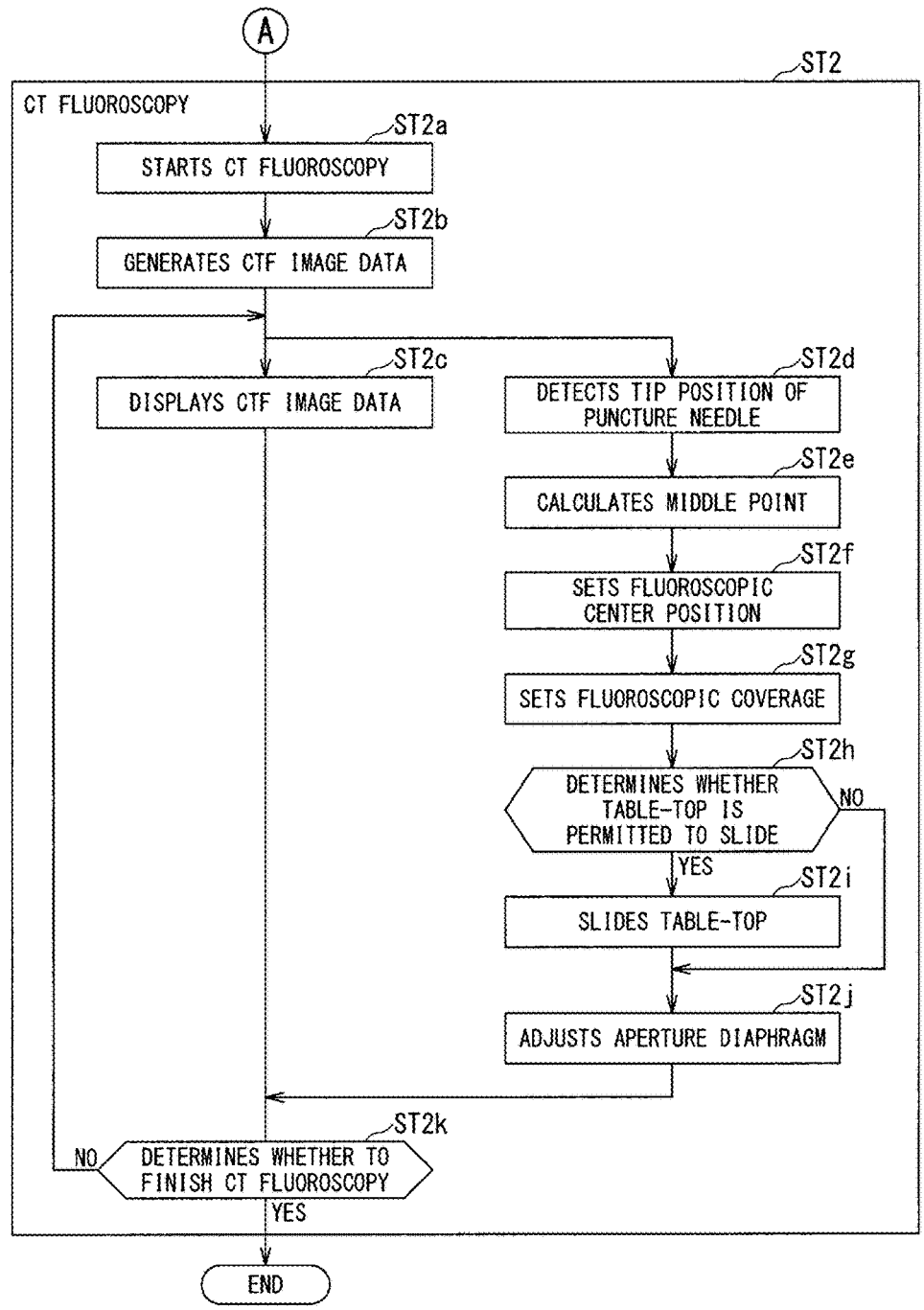
Figure 15:
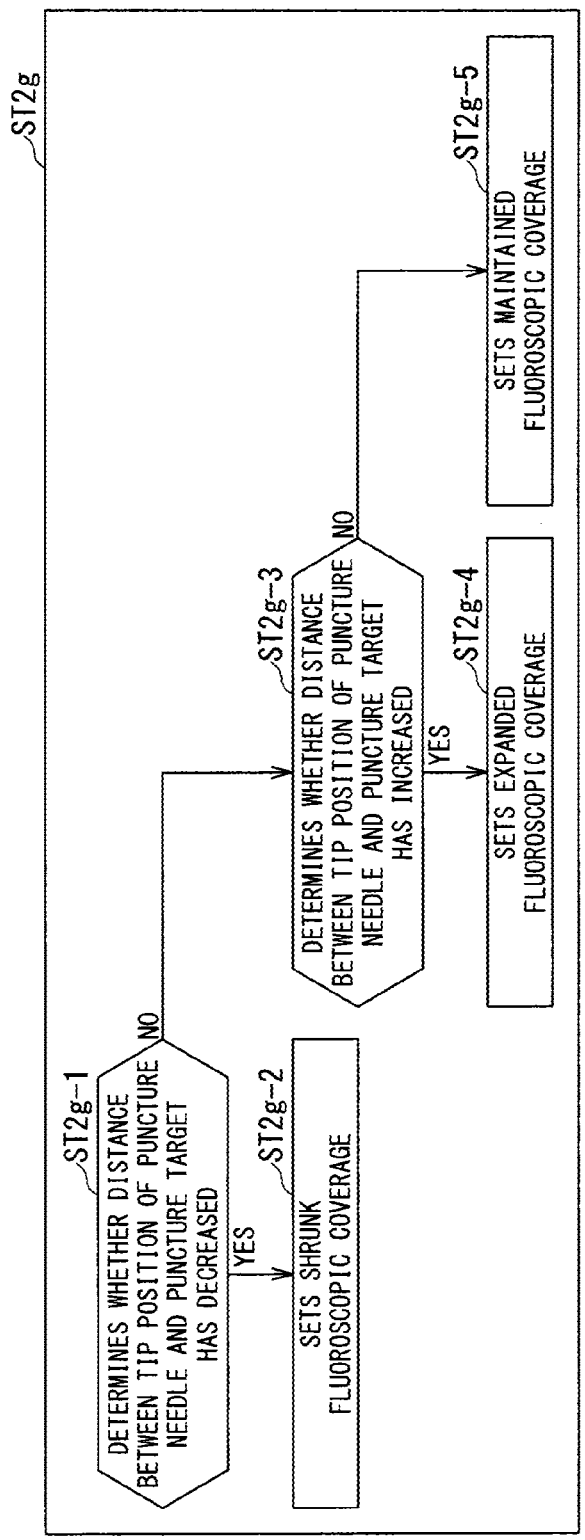

Next, operation of the X-ray CT apparatus 1 according to the present embodiment will be described using FIG. 1 and FIGS. 13 to 15. FIGS. 13 to 15 show an operation for obtaining CTF image data using the fluoroscopy condition setting method illustrated in FIGS. 10A to 10C.

FIGS. 13 to 15 are flowcharts illustrating the operation of the X-ray CT apparatus 1 according to the present embodiment.

To describe FIG. 13, the X-ray CT apparatus 1 works out a puncture plan after the patient O is placed on the table-top 30 (step ST1). During the puncture planning, the X-ray CT apparatus 1 sets a fluoroscopic center position and fluoroscopic coverage (step ST1a). Then, in step ST1b, by controlling the scanner 11 via the controller 32, the X-ray CT apparatus 1 slides the table-top 30, on which the patient O is placed, left or right, up or down based on the fluoroscopic center position set in step ST1a. Furthermore, in step ST1c, the X-ray CT apparatus 1 adjusts the aperture of the diaphragm 22 by controlling the scanner 11 via the controller 32 based on the fluoroscopic coverage set in step ST1a. Note that the operations of steps ST1b and ST1c may be carried out in random order or simultaneously.

Then, the X-ray CT apparatus 1 performs CT imaging (step ST1d). In so doing, the fluoroscopic center position established by sliding in step ST1b is used as an imaging center position P while the fluoroscopic coverage based on the aperture of the diaphragm 22 adjusted in step ST1c is used as radiographic coverage. Then, in step ST1e, the X-ray CT apparatus 1 generates single-shot CT image data as a result of the CT imaging performed in step ST1d. On the single-shot CT image displayed based on the single-shot CT image data generated in step ST1e, the X-ray CT apparatus 1 sets an insert point on skin surface and a puncture target according to input from the input device 44 (step ST1f).

Referring now to FIG. 14, the X-ray CT apparatus 1 performs CT fluoroscopy with the patient O placed on the table-top 30 (step ST2). In step ST2a, with the table-top 30 placed at the position established by the sliding in step ST1b, the X-ray CT apparatus 1 starts CT fluoroscopy using the X-ray irradiation coverage resulting from the aperture adjustment of the diaphragm 22 in step ST1c. The X-ray CT apparatus 1 generates CTF image data of the frame FL[t] in real time t by CT fluoroscopy (step ST2b) and displays the CTF image data as a CTF image on the display 45 in real time (step ST2c). During the CT fluoroscopy started in step ST2a, when the operator punctures the patient O, an image of the puncture needle is placed in the CTF image data of the frame FL[t] (illustrated in FIGS. 11A to 11E and FIG. 12).

In step ST2d, concurrently with the operation of step ST2c, the X-ray CT apparatus 1 detects the tip position of the puncture needle in the frame FL[t]. Then, in step ST2e, the X-ray CT apparatus 1 calculates the middle point of the line segment between the tip position of the puncture needle detected in step ST2d and the position corresponding to the position of the puncture target T set in step ST1f (illustrated in FIG. 4). In step ST2f, the X-ray CT apparatus 1 sets the middle point calculated in step ST2e, as a fluoroscopic center position in the next frame FL[t+1]. Moreover, in step ST2g, the X-ray CT apparatus 1 sets the fluoroscopic coverage in the next frame FL[t+1] based on the middle point calculated in step ST2e.

Moving to FIG. 15, in step ST2g, the X-ray CT apparatus 1 determines whether or not the distance between the tip position of the puncture needle and puncture target in the frame FL[t] has decreased compared to the distance between the tip position of the puncture needle and puncture target in the previous frame FL[t−1], i.e., whether or not the puncture needle has moved toward the puncture target (step ST2g-1). If the result of determination in step ST2g-1 is YES, i.e., if it is determined that the distance between the tip position of the puncture needle and puncture target in the frame FL[t] has decreased, the X-ray CT apparatus 1 sets a shrunk fluoroscopic coverage for the next frame FL[t+1] (step ST2g-2).

On the other hand, if the result of determination in step ST2g-1 is NO, i.e., if it is determined that the distance between the tip position of the puncture needle and puncture target in the frame FL[t] has not decreased, the X-ray CT apparatus 1 determines whether or not the distance between the tip position of the puncture needle and puncture target in the frame FL[t] has increased compared to the distance between the tip position of the puncture needle and puncture target in the previous frame FL[t−1], i.e., whether or not the puncture needle has moved away from the puncture target (step ST2g-3). If the result of determination in step ST2g-3 is YES, i.e., if it is determined that the distance between the tip position of the puncture needle and puncture target in the frame FL[t] has increased, the X-ray CT apparatus 1 sets an expanded fluoroscopic coverage for the next frame FL[t+1] (step ST2g-4).

On the other hand, if the result of determination in step ST2g-3 is NO, i.e., if it is determined that the distance between the tip position of the puncture needle and puncture target in the frame FL[t] has not increased, the X-ray CT apparatus 1 sets the maintained fluoroscopic coverage for the next frame FL[t+1] (step ST2g-5). Note that since a specific method of step ST2g has already been described using FIGS. 9A and 9B, description thereof will be omitted here.

Returning to the description of FIG. 14, in step ST2h, the X-ray CT apparatus 1 determines whether or not the table-top 30 on which the patient O is placed is permitted to slide during the CT fluoroscopy started in step ST2a. If the result of determination in step ST2h is YES, i.e., if it is determined that the table-top 30 is permitted to slide during the CT fluoroscopy, the X-ray CT apparatus 1 slides the table-top 30, on which the patient O (illustrated in FIG. 1) is placed, left or right, up or down (step ST2i) by controlling the scanner 11 via the controller 32 based on the fluoroscopic center position set in step ST2f for the next frame FL[t+1].

On the other hand, if the result of determination in step ST2h is NO, i.e., if it is determined that the table-top 30 is not permitted to slide during the CT fluoroscopy, the X-ray CT apparatus 1 adjusts the aperture of the diaphragm 22 by controlling the scanner 11 via the controller 32 based on the fluoroscopic coverage set in step ST2g for the next frame FL[t+1] (step ST2j).

Next, in step ST2k, the X-ray CT apparatus 1 determines whether to finish the CT fluoroscopy started in step ST2a. If the result of determination in step ST2k is YES, i.e., if it is determined that the CT fluoroscopy is to be finished, the X-ray CT apparatus 1 finishes the operation. On the other hand, if the result of determination in step ST2k is NO, i.e., if it is determined that the CT fluoroscopy is not to be finished, the X-ray CT apparatus 1 generates CTF image data of the next frame FL[t+1] through CT fluoroscopy (step ST2b) and displays the CTF image data as a CTF image on the display 45 in real time (step ST2c). Concurrently with this, the X-ray CT apparatus 1 detects the tip position of the puncture needle in the frame FL[t+1] (step ST2d) and calculates the middle point of the line segment between the tip position and the position corresponding to the position of the puncture target T set in step ST1f (illustrated in FIG. 4) (step ST2e).

Figure 16:
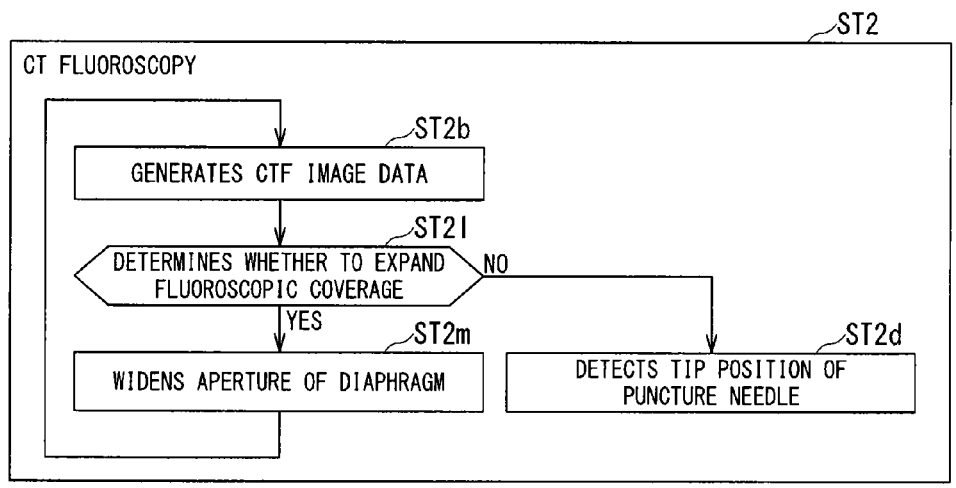
FIG. 16 is a flowchart illustrating a variation of an operation of the X-ray CT apparatus according to the present embodiment.

FIG. 16 is a flowchart illustrating a variation of the operation of the X-ray CT apparatus 1 according to the present embodiment.

After step ST2b, concurrently with the operation of step ST2c, the X-ray CT apparatus 1 determines whether to expand the fluoroscopic coverage for the next frame FL[t+1] (step ST2l). The determination in step ST2l is made based on whether or not a command to expand the fluoroscopic coverage has been entered via the input device 44 and/or whether or not an expansion timing has come according to predetermined time intervals.

If the result of determination in step ST2l is YES, i.e., if it is determined that the fluoroscopic coverage is to be expanded for the next frame FL[t+1], the X-ray CT apparatus 1 widens the aperture of the diaphragm 22 to a desired size for the next frame FL[t+1] by controlling the scanner 11 via the controller 32 (step ST2m). Then, the X-ray CT apparatus 1 returns to the operation of step ST2b. Note that the fluoroscopic coverage expanded in step ST2m may be maintained over plural frames.

If the result of determination in step ST2l is NO, i.e., if it is determined that the fluoroscopic coverage is not to be expanded for the next frame FL[t+1], the X-ray CT apparatus 1 returns to the operation of step ST2d.

(Dealing with Displaced Tip Position of Puncture Needle)

A case in which the fan angle of the X-rays emitted from the X-ray tube 21 is changed using the diaphragm 22 has been described above. Next, description will be given of a case in which the cone angle of the X-rays emitted from the X-ray tube 21 is changed using the diaphragm 22.

During CT fluoroscopy, the tip position of the puncture needle may sometimes get displaced due to body movements and the like of the patient O on the table-top 30. Thus, fluoroscopy condition setting unit 41e detects and tracks the tip position of the puncture needle using a magnetic sensor or CT fluoroscopic images, and thereby detects displacement of the patient O in the Z direction. Then, the mechanism control unit 41f temporarily expands the cone angle of X-rays by controlling the aperture of the diaphragm 22.

Figures 17A, 17B, 17C:
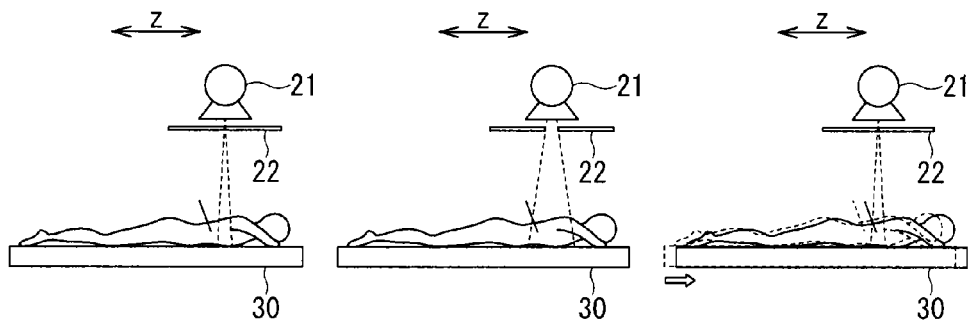
FIGS. 17A to 17C are diagrams for describing a relationship between a displacement of a tip position of the puncture needle and a cone angle of X-rays.

FIGS. 17A to 17C are diagrams for describing a relationship between the displacement of the tip position of the puncture needle and the cone angle of X-rays.

During CT fluoroscopy, it is detected that the tip position of the puncture needle does not exist in the X-ray irradiation coverage illustrated in FIG. 17A. Next, as the aperture of the diaphragm 22 is controlled, the cone angle is increased as illustrated in FIG. 17B (the number of slices is increased). Next, the table-top 30 is slid in the Z direction so as to place the tip position of the puncture needle at a center of the cone angle and the aperture of the diaphragm 22 is controlled, thereby decreasing the cone angle so as to include the tip position of the puncture needle.

Furthermore, the fluoroscopy condition setting unit 41e can detect the displacement of the patient O in the X direction based on a differential value among CTF images in plural frames. When the differential value is equal to or larger than a threshold, the fluoroscopy condition setting unit 41e determines that the patient O is displaced in the X direction. In that case, the mechanism control unit 41f temporarily expands the fan angle of X-rays by controlling the aperture of the diaphragm 22, updates a CTF image related to a background image, and then returns the fan angle to its pre-expansion state.

(Spatial Resolution of CTF Image)

In a CTF image portion contained in superimposed images illustrated in FIGS. 11C and 11E, a spatial resolution is improved over a background image portion contained in the superimposed images because of the reduced fluoroscopic coverage.

Figure 18:
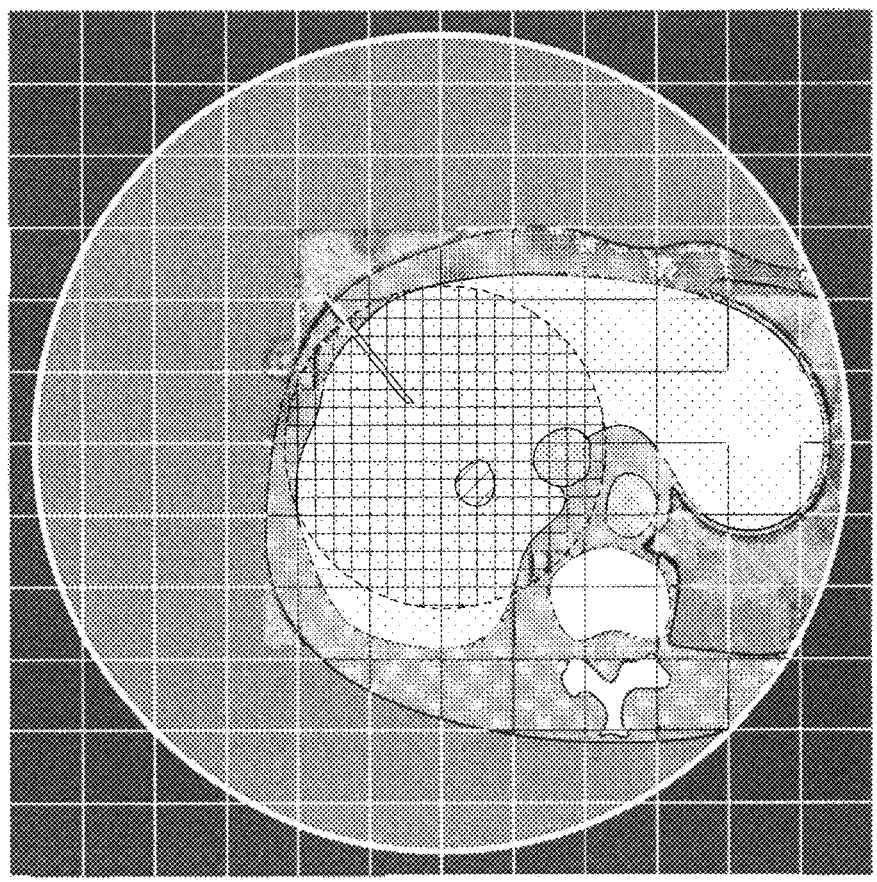
FIG. 18 is a diagram for describing a spatial resolution of a CTF image.

FIG. 18 is a diagram for describing the spatial resolution of a CTF image.

As illustrated in FIG. 18, in the CTF image portion, each pixel having a CT value is smaller in size than in the background image portion. Thus, when the superimposed image illustrated in FIG. 18 is displayed on the display of the display 45, the CTF image portion contained in the superimposed image has higher fidelity than does the background image portion.

With the X-ray CT apparatus 1 according to the present embodiment, since a part which is located outside a periphery of the puncture needle tip and irrelevant to the puncture procedure is not subjected to fluoroscopy, health hazards to the patient can be reduced. Besides, the X-ray CT apparatus 1 according to the present embodiment uses past images to display the part which is located outside the periphery of the puncture needle tip and irrelevant to the puncture procedure, and consequently can also present geometry of the part to the operator.

In particular, with the X-ray CT apparatus 1, since the part which is located outside the periphery of the puncture needle tip and irrelevant to the puncture procedure is not irradiated with X-rays, radiation exposure of the patient caused by CT fluoroscopy can be reduced.

While certain embodiments have been described, these embodiments have been presented by way of example only, and are not intended to limit the scope of the inventions. Indeed, the novel methods and systems described herein may be embodied in a variety of other forms; furthermore, various omissions, substitutions and changes in the form of the methods and systems described herein may be made without departing from the spirit of the inventions. The accompanying claims and their equivalents are intended to cover such forms or modifications as would fall within the scope and spirit of the inventions.

What is claimed is:

1. An X-ray CT apparatus comprising:
   a table-top on which an object is able to be placed;
   an X-ray tube configured to emit X-rays around the table-top;
   a detector configured to detect the X-rays and output a detection signal; and
   processing circuitry, wherein
   the processing circuitry is configured to:
      reconstruct a CT image based on the detection signal;
      set a field of view based on positions of a puncture needle and a puncture target on the CT image;
      control an X-ray irradiation coverage based on the field of view, the X-ray irradiation coverage being an area irradiated with the X-rays;
      emit X-rays whose the X-ray irradiation coverage is controlled;
      output the detection signal based on the controlled X-rays;
      superimpose the CT image in the field of view reduced in size, on the CT image in the field of view expanded in size;
      put graphics of the puncture needle in a portion outside the CT image in the reduced field of view, and inside the CT image in the expanded field of view; and
      display the superimposed image and the graphics on a display.

2. The X-ray CT apparatus according to claim 1, wherein the processing circuitry is configured to control the X-ray irradiation coverage by moving a position of a collimator configured to limit the X-ray irradiation coverage.

3. The X-ray CT apparatus according to claim 1, wherein the processing circuitry is configured to:
   set an imaging center position, which is a center position of the field of view, together with the field of view; and
   control an X-ray irradiation center, which is a center at which the X-rays are directed, based on the imaging center position.

4. The X-ray CT apparatus according to claim 3, wherein the processing circuitry is configured to control the X-ray irradiation center by sliding the table-top.

5. The X-ray CT apparatus according to claim 4, wherein the processing circuitry is configured to set the position of the puncture target as the imaging center position.

6. The X-ray CT apparatus according to claim 4, wherein the processing circuitry is configured to:
   detect a tip position of the puncture needle based on the CT image in a previous frame; and
   set a middle point between the tip position of the puncture needle and the puncture target as the imaging center position in a subsequent frame.

7. The X-ray CT apparatus according to claim 6, wherein the processing circuitry is configured to:
   set the field of view in the subsequent frame narrower than the field of view in the previous frame;
   superimpose the CT image in the subsequent frame on the CT image in the previous frame; and
   display a resulting CT image on the display.

8. The X-ray CT apparatus according to claim 7, wherein the processing circuitry is configured to:
   superimpose the CT image in the subsequent frame on the CT image in the previous frame, when it is determined that the field of view in the subsequent frame is smaller than a threshold; and display a resulting CT image on the display.

9. The X-ray CT apparatus according to claim 6, wherein the processing circuitry is configured to detect the tip position of the puncture needle based on the CT image in the previous frame.

10. A display method for CT image comprising:

emitting X-rays around the table-top on which an object is able to be placed;

detecting the X-rays and outputting a detection signal;

reconstructing a CT image based on the detection signal;

setting a field of view based on positions of a puncture needle and a puncture target on the CT image;

controlling an X-ray irradiation coverage based on the field of view, the X-ray irradiation coverage being an area irradiated with the X-rays;

emitting X-rays whose the X-ray irradiation coverage is controlled;

outputting the detection signal based on the controlled X-rays;

superimposing the CT image in the field of view reduced in size, on the CT image in the field of view expanded in size;

putting graphics of the puncture needle in a portion outside the CT image in the reduced field of view, and inside the CT image in the expanded field of view; and displaying the superimposed image and the graphics on a display.

\* \* \* \* \*